United States Statutory Invention Registration [19]

[11] Reg. Number: H991

Fischer et al.

[43] Published: Nov. 5, 1991

[54] SYNTHESIS OF NITRATOMETHYLMETHYLOXETANE (NMMO)

[75] Inventors: John W. Fischer; Richard A. Hollins, both of Ridgecrest, Calif.

[73] Assignee: The United States of America as represented by the Secretary of the Navy, Washington, D.C.

[21] Appl. No.: 296,556

[22] Filed: Jan. 3, 1989

[51] Int. Cl.[5] ..... C07D 305/04
[52] U.S. Cl. ..... 549/510
[58] Field of Search ..... 549/510

[56] References Cited

U.S. PATENT DOCUMENTS 3,058,994 10/1962 Schrage ..... 260/333
4,560,779 12/1985 Guimont et al. ..... 549/510

OTHER PUBLICATIONS

Morton-Thiokol, Inc., "High Energy Binders Final Report", Jun. 1985, pp. 8 and 82, Publication 85837.

*Primary Examiner*—Robert L. Stoll
*Assistant Examiner*—Joseph D. Anthony
*Attorney, Agent, or Firm*—Sol Sheinbein; Melvin J. Sliwka; Stuart H. Nissim

[57] ABSTRACT

A method of preparing 3-nitratomethyl-3-methyloxetane.

16 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SYNTHESIS OF NITRATOMETHYLMETHYLOXETANE (NMMO)

BACKGROUND OF THE INVENTION

1. Field of the Invention

This invention relates to high energy propellant binders and explosive formulations. More particularly, this invention relates to a method of preparing 3-nitratomethyl-3-methyloxetane (NMMO) that is superior to previously known methods of making 3-nitratomethyl-3-methyloxetane. 3-nitratomethyl-3-methyloxetane is useful as an ingredient in high energy propellant binders and certain explosive formulations.

2. Description of the Prior Art

High energy propellant binders have been extensively investigated as a means of increasing the energy and performance of missile propellants over those currently in use. A very promising candidate for a new highly energetic binder system contains 3-nitratomethyl-3-methyloxetane. However, 3-nitratomethyl-3-methyloxetane is currently available only in limited quantities.

The prior art method for making 3-nitratomethyl-3-methyloxetane requires the use of very corrosive and difficult to handle materials. In the prior art, acetylnitrate is used to nitrate hydroxymethylmethyloxetane (HMMO) to produce 3-nitratomethyl-3-methyloxetane. Prior art requires the preparation of acetylnitrate by reacting acetic anhydride with concentrated nitric acid. Acetylnitrate is a very hazardous, unstable explosive that can detonate spontaneously in storage which makes large scale commercial manufacture of 3-nitratomethyl-3-methyloxetane difficult and hazardous. Furthermore, 3-nitratomethyl-3-methyloxetane produced by this method must be purified by the tedious technique of chromatography.

SUMMARY OF THE INVENTION

This invention eliminates the use of both nitric acid and acetylnitrate in the production of 3-nitratomethyl-3-methyloxetane. Moreover, the 3-nitratomethyl-3-methyloxetane produced by this method is of high purity, eliminating the need for chromatography. This invention is also amenable to large scale commercial manufacture of 3-nitratomethyl-3-methyloxetane.

An object of this invention is to provide a simple and efficient method of preparing 3-nitratomethyl-3-methyloxetane by the direct liquid phase nitration of hydroxymethylmethyloxetane using dinitrogen pentoxide ($N_2O_5$) as the nitrating agent.

A further object of this invention is to provide a method for economical commercial production of 3-nitratomethyl-3-methyloxetane that has a high yield and high purity.

DESCRIPTION OF THE PREFERRED EMBODIMENT

The starting material is hydroxymethylmethyloxetane. Hydroxymethylmethyloxetane is dissolved in dry chloroform and set aside. Dinitrogen pentoxide ($N_2O_5$) is then prepared by a known reaction wherein commercially available dinitrogen tetroxide ($N_2O_4$) gas is contacted with dry ozone until all of the red $N_2O_4$ is consumed. See Guye, P. A., U.S. Pat. No. 1,348,873 (1920) for the $N_2O_5$ procedure. The resulting $N_2O_5$ is captured in solid form in dry ice.

The $N_2O_5$ is then dissolved in dry chloroform to make a solution. The $N_2O_5$ in solution is then slowly added, using a dropping funnel, to the prepared hydroxymethylmethyloxetane solution while the solution is continually stirred. Stirring continues for about 2 hours after the last of the $N_2O_5$ solution has been added to the hydroxymethylmethyloxetane solution. At this point the reaction is complete and the solution contains 3-nitratomethyl-3-methyloxetane. The $N_2O_5$ also may be dissolved in carbon tetrachloride, methylene chloride or acetonitrile as substitutes for the dry chloroform.

The solution is then, in succession, washed with distilled water, then with saturated sodium bicarbonate solution, and then with saturated sodium chloride solution. Water is then removed from the chloroform and 3-nitratomethyl-3-methyloxetane solution by adding anhydrous sodium sulfate. After 10 minutes the sodium sulfate is removed by filtration. The chloroform is then removed under reduced pressure leaving almost pure 3-nitratomethyl-3-methyloxetane. The resulting 3-nitratomethyl-3-methyloxetane can be further purified by vacuum distillation.

The preferred embodiment of this invention may be further understood by referring to the following examples. These examples are given to illustrate but not limit this invention.

EXAMPLE 1

The starting material, 15 g (150 mmol) hydroxymethylmethyloxetane, was dissolved in 300 milliliters of dry chloroform at 0° C., at atmospheric pressure and set aside.

Dinitrogen pentoxide ($N_2O_5$) was then prepared by contacting commercially available dinitrogen tetroxide ($N_2O_4$) with dry ozone at ambient temperature and pressure until all of the red dinitrogen tetroxide was consumed. The resulting dinitrogen pentoxide ($N_2O_5$), 32.4 g, was captured in solid form in a dry ice trap at −78° C.

The 32.4 g of dinitrogen pentoxide ($N_2O_5$) was then dissolved in dry chloroform at 0° C., at atmospheric pressure, to make a 1 Molar solution, approximately 300 milliliters.

The 300 ml of 1 Molar solution of dinitrogen pentoxide ($N_2O_5$) was then slowly added to the prepared hydroxymethylmethyloxetane solution over a 20 minute period using a dropping funnel while stirring continuously. After the addition was completed, the resulting solution was stirred continuously for 2 hours while maintaining the temperature at 0 degrees C. with an ice bath. The solution contained 3-nitratomethyl-3-methyloxetane.

The solution was then washed, in succession, with 250 ml of distilled water, then 250 ml of aqueous saturated sodium bicarbonate solution, and then 250 ml of aqueous saturated sodium chloride solution. Water is then removed from the chloroform and 3-nitratomethyl-3-methyloxetane solution by adding 2 g of anhydrous sodium sulfate. After ten minutes the sodium sulfate was removed by filtration. The chloroform was then removed using a rotary evaporator under reduced pressure, 14 torr, leaving almost pure 3-nitratomethyl-3-methyloxetane.

The 3-nitratomethyl-3-methyloxetane was then purified by vacuum distillation at 0.35 torr at a temperature range between 52 and 62 degrees C. 20 grams of 99% pure 3-nitratomethyl-3-methyloxetane were obtained. NMR showed very clean product. Yield was 91%.

EXAMPLE 2

20 ml of 1 molar dinitrogen pentoxide ($N_2O_5$) in dry chloroform was added drop-wise with a dropping funnel over five minutes to a continuously stirred solution of 1 gram of hydroxymethylmethyloxetane in 20 ml of dry chloroform held at 0° C. with an ice-water bath. The solution was then continuously stirred at 0° C. for an additional one and one-half hours. The solution was next washed in succession with 100 ml of water, then 100 ml of aqueous saturated sodium bicarbonate solution, and then 100 ml of aqueous saturated sodium chloride solution. The solution was then dried by adding 1 g of anhydrous sodium sulfate. After 10 minutes the sodium sulfate was removed by filtration. Chloroform was then removed by using a rotary evaporator at 14 torr, yielding 1.5 grams of 3-nitratomethyl-3-methyloxetane.

What is claimed is:

1. A method of preparing 3-nitratomethyl-3-methyloxetane comprising the following steps:

dissolving hydroxymethylmethyloxetane in a solvent;

dissolving dinitrogen pentoxide in a solvent;

adding said dinitrogen pentoxide solutions to said hydroxymethylmethyloxetane solution;

holding said reaction mixture at a first reaction temperature;

stirring said reaction mixture for a time sufficient to complete the reaction while holding said reaction mixture at said first reaction temperature;

washing said reaction mixture with water;

washing said reaction mixture with saturated sodium bicarbonate solution;

washing said reaction mixture with saturated sodium chloride solution;

drying said reaction mixture with anhydrous sodium sulfate;

filtering said sodium sulfate from said reaction mixture;

removing said solvent at reduced pressure;

purifying said 3-nitratomethyl-3-methyloxetane by vacuum distillation; and holding said product at a second reaction temperature while purifying.

2. The method of claim 1 wherein said solvent used to dissolve said dinitrogen pentoxide is dry chloroform.

3. The method of claim 1 wherein said solvent to dissolve said dinitrogen pentoxide is selected from the group consisting of methylene chloride, carbon tetrachloride, or acetonitrile.

4. The method of claim 1 wherein said first reaction temperature is from about −15° to +5° C.

5. The method of claim 1 wherein said first reaction temperature is 0° C.

6. The method of claim 1 wherein said stirring is a continuous stirring action.

7. The method of claim 1 wherein said time for completion of the reaction is from about one and one-half to two hours.

8. The method of claim 1 wherein said water for washing said reaction mixture is about 50% to 250% of the volume of said reaction mixture.

9. The method of claim 1 wherein said saturated sodium bicarbonate solution for washing said reaction mixture is about 50% to 250% of the volume of said reaction mixture.

10. The method of claim 1 wherein said sodium chloride solution for washing said reaction mixture is about 50% to 250% of the volume of said reaction mixture.

11. The method of claim 1 wherein said sodium sulfate for drying said reaction mixture is about 1 to 2 grams.

12. The method of claim 1 wherein said filtrating of said sodium sulfate is about ten minutes after adding said sodium sulfate.

13. The method of claim 1 wherein said reduced pressure for removing said solvent is about 14 torr.

14. The method of claim 1 wherein said vacuum distillation for purifying is at 0.35 torr.

15. The method of claim 1 wherein said second reaction temperature is from about 52° to 62° C.

16. The method of claim 1 wherein said solvent used to dissolve said hydroxymethylmethyloxetane is dry chloroform.

* * * * *